(12) United States Patent
Kono et al.

(10) Patent No.: US 12,074,286 B2
(45) Date of Patent: Aug. 27, 2024

(54) ADDITIVE FOR NONAQUEOUS ELECTROLYTE SOLUTIONS, NONAQUEOUS ELECTROLYTE SOLUTION, AND ELECTRICITY STORAGE DEVICE

(71) Applicant: SUMITOMO SEIKA CHEMICALS CO., LTD., Hyogo (JP)

(72) Inventors: Yuki Kono, Hyogo (JP); Yasuyuki Takai, Hyogo (JP); Koji Fujita, Hyogo (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 886 days.

(21) Appl. No.: 17/041,341

(22) PCT Filed: Jan. 22, 2019

(86) PCT No.: PCT/JP2019/001880
§ 371 (c)(1),
(2) Date: Sep. 24, 2020

(87) PCT Pub. No.: WO2019/187545
PCT Pub. Date: Oct. 3, 2019

(65) Prior Publication Data
US 2021/0367269 A1    Nov. 25, 2021

(30) Foreign Application Priority Data
Mar. 30, 2018   (JP) .................. 2018-067264

(51) Int. Cl.
*H01M 10/0567* (2010.01)
*H01G 11/06* (2013.01)
(Continued)

(52) U.S. Cl.
CPC ........ *H01M 10/0567* (2013.01); *H01G 11/06* (2013.01); *H01G 11/64* (2013.01);
(Continued)

(58) Field of Classification Search
None
See application file for complete search history.

(56) References Cited

U.S. PATENT DOCUMENTS 3,106,565 A * 10/1963 Newallis ........... C07F 9/655345
549/8
3,288,671 A   11/1966 Greenbaum
(Continued)

FOREIGN PATENT DOCUMENTS

CN        103709568        4/2014
EP         3349290         7/2018
(Continued)

OTHER PUBLICATIONS

Machine translation of KR 20130120172 A (Year: 2013).*
(Continued)

*Primary Examiner* — Robert S Carrico
(74) *Attorney, Agent, or Firm* — HSML P.C.

(57) ABSTRACT

(1a)

(1b)

(Continued)

Disclosed is an additive for nonaqueous electrolyte solutions, including a compound represented by Formula (1a) or (1b).
In Formulae (1a) and (1b), Z represents a monovalent group represented by Formula (2a), (2b), or (2c).

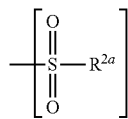

(2a)

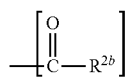

(2b)

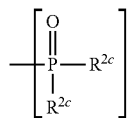

(2c)

13 Claims, 1 Drawing Sheet

(51) Int. Cl.
  *H01G 11/64* (2013.01)
  *H01M 10/0525* (2010.01)
  *H01M 10/0568* (2010.01)
  *H01M 10/0569* (2010.01)
  *H01M 10/42* (2006.01)
(52) U.S. Cl.
  CPC ... *H01M 10/0525* (2013.01); *H01M 10/0568* (2013.01); *H01M 10/0569* (2013.01); *H01M 10/4235* (2013.01); *H01M 2300/0037* (2013.01)

(56) References Cited

U.S. PATENT DOCUMENTS

| | | | |
|---|---|---|---|
| 3,357,996 A | * | 12/1967 | Cobb ............... C07D 333/48 252/364 |
| 3,574,512 A | * | 4/1971 | Weber ............... C07D 333/48 8/510 |
| 3,983,134 A | | 9/1976 | Matsui et al. |
| 4,619,924 A | | 10/1986 | Hamanaka |
| 2017/0271715 A1 | | 9/2017 | Kim et al. |

FOREIGN PATENT DOCUMENTS

| | | |
|---|---|---|
| FR | 2281366 | 3/1976 |
| JP | S51-019785 A | 2/1976 |
| JP | S63-102173 | 5/1988 |
| JP | H5-074486 | 3/1993 |
| JP | H10-050342 | 2/1998 |
| JP | 2012-056925 | 3/2012 |
| JP | 2012-106987 | 6/2012 |
| JP | 2016-192357 | 11/2016 |
| JP | 2016-192358 | 11/2016 |
| JP | 2016-192360 | 11/2016 |
| JP | 2016-192362 | 11/2016 |
| JP | 2017-208322 | 11/2017 |
| KR | 20130120172 A * | 11/2013 |
| TW | 201639225 | 11/2016 |
| WO | 2017/043576 | 3/2017 |
| WO | 2018/016195 | 1/2018 |

OTHER PUBLICATIONS

B. Li et al, "One-Step Synthesis of 3-Thioacetylsulfolane", SYNLETT, vol. 2012, No. 01, Dec. 5, 2011, p. 131-p. 133, XP055869454.
The extended European search report issued for European Patent Application No. 19775625.7, Dec. 17, 2021, 11 pages.
International Preliminary Report on Patentability issued for PCT/JP2019/001880, Oct. 15, 2020, 6 pages.
International Search Report of PCT/JP2019/001880, Apr. 23, 2019, 2 pages.

* cited by examiner

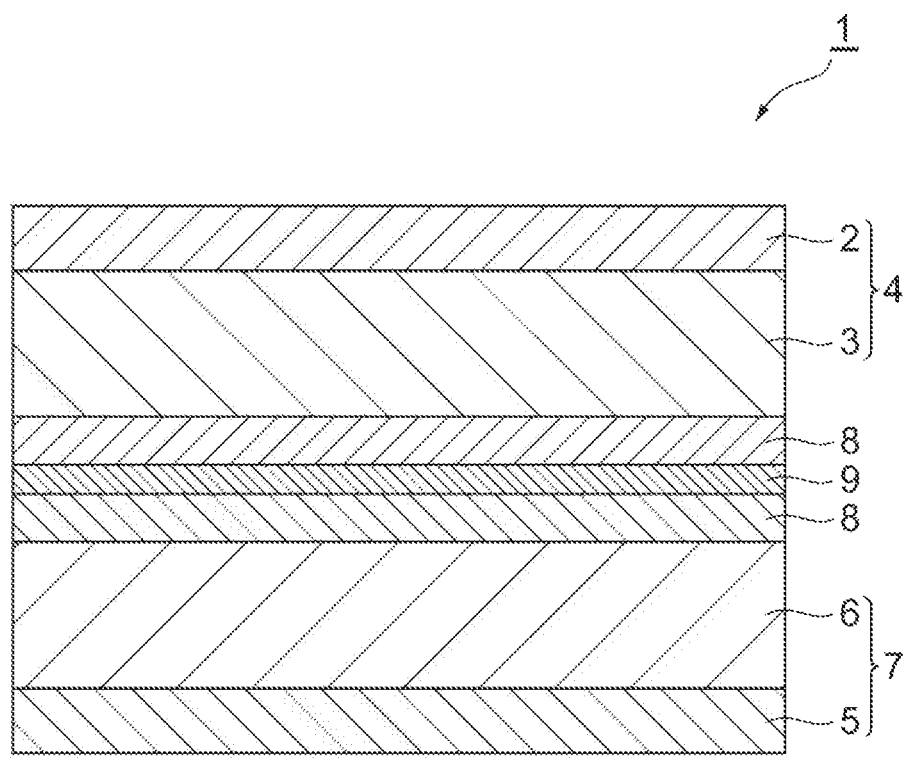

ADDITIVE FOR NONAQUEOUS ELECTROLYTE SOLUTIONS, NONAQUEOUS ELECTROLYTE SOLUTION, AND ELECTRICITY STORAGE DEVICE

TECHNICAL FIELD

The present invention relates to an additive for nonaqueous electrolyte solutions. The present invention further relates to a nonaqueous electrolyte solution containing the additive for nonaqueous electrolyte solutions and an electricity storage device using the nonaqueous electrolyte solution.

BACKGROUND ART

In recent years, along with an increase in attention to solving environmental problems and establishing a sustainable recycling-based society, nonaqueous electrolyte solution secondary batteries typified by lithium ion batteries and electricity storage devices such as an electric double layer capacitor have been widely studied. Among those, the lithium ion batteries are used as power sources for laptops, mobile phone, or the like from the viewpoint that they have high working voltages and energy densities. These lithium ion batteries are expected as a new power source from the viewpoint that they have higher energy densities than lead batteries and nickel-cadmium batteries, and a higher capacity of batteries is realized therewith. However, the lithium ion batteries have a problem in that the capacity of the batteries is reduced over time in charge/discharge cycles.

As a method for suppressing a reduction in the capacity of a battery over time in charge/discharge cycles, a method in which various additives are added to an electrolyte solution has been examined. The additives are decomposed during a first charge/discharge to form a film called a solid electrolyte interface (SEI) on a surface of an electrode. Since the SEI is formed during the first cycle of the charge/discharge cycles, electricity is not consumed for decomposition of a solvent and the like in the electrolyte solution, the lithium ions can be transferred between electrodes through the SEI. That is, formation of the SEI prevents the deterioration of electricity storage devices such as a nonaqueous electrolyte solution secondary battery in a case where the charge/discharge cycles are repeated, and thus contributes to an improvement of battery characteristics, storage characteristics, load characteristics, or the like.

For example, Patent Literature 1 discloses that charge/discharge cycle characteristics of a lithium secondary battery are improved by addition of 1,3-propanesultone (PS) into an electrolyte solution that forms SEI as an additive. Further, Patent Literature 2 discloses that the self-discharge rate of a nonaqueous electrolyte secondary battery is reduced by addition of a 1,3,2-dioxaphospholane-2-dioxide derivative or PS as an additive into an electrolyte solution. Patent Literature 3 discloses that discharge characteristics and the like of a lithium secondary battery are improved by adding a derivative of vinylene carbonate (VC) as an additive.

CITATION LIST

Patent Literature

[Patent Literature 1] Japanese Unexamined Patent Publication No. S63-102173

[Patent Literature 2] Japanese Unexamined Patent Publication No. H10-50342

[Patent Literature 3] Japanese Unexamined Patent Publication No, H05-074486

SUMMARY OF INVENTION

Technical Problem

However, even with use of those additives, sufficient performance has not been obtained and there has been a desire for development of novel additives for further improving battery characteristics of electricity storage devices. In addition, the electrolyte solution in which a derivative of VC is used as an additive as described in Patent Literature 3 generates gases including carbon dioxide upon decomposition of the derivative of VC on an electrode, which thus leads to a reduction in battery performance.

An object of the present invention is to provide an additive for nonaqueous electrolyte solutions, which makes it possible to suppress initial resistance, improve cycle characteristics over a long period of time, and suppress gas generation in a case where the additive for nonaqueous electrolyte solutions is used in an electricity storage device such as a nonaqueous electrolyte solution secondary battery. In addition, another object of the present invention is to provide a nonaqueous electrolyte solution using the additive for nonaqueous electrolyte solutions and an electricity storage device using the nonaqueous electrolyte solution.

Solution to Problem

In an aspect of the present invention, an additive for nonaqueous electrolyte solutions, including a compound represented by the following Formula (1a) or Formula (1b) is provided.

(1a)

(1b)

In Formulae (1a) and (1b), X represents an alkylene group having 3 to 7 carbon atoms, which may be substituted, or an alkenylene group having 3 to 7 carbon atoms, which may be substituted, each of which constitutes a cyclic structure together with the sulfur atom of a sulfonyl group, n represents an integer of 1 to 7, Z represents a monovalent group represented by Formula (2a), (2b), or (2c), and in represents 0 or 1.

(2a)

-continued

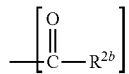   (2b)

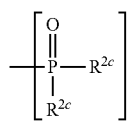   (2c)

$R^{2a}$, $R^{2b}$, and $R^{2c}$ in Formulae (2a), (2b), and (2c) each independently represent an alkyl group having 1 to 4 carbon atoms, which may be substituted, an alkenyl group having 2 to 4 carbon atoms, which may be substituted, an alkynyl group having 2 to 4 carbon atoms, which may be substituted, an aryl group which may be substituted, an alkoxy group having 1 to 4 carbon atoms, which may be substituted, an alkenyloxy group having 2 to 4 carbon atoms, which may be substituted, an alkynyloxy group having 2 to 4 carbon atoms, which may be substituted, an aryloxy group which may be substituted, a hydroxyl group, a lithium alcoholate group, or a lithium atom, and two $R^{2c}$'s in the same molecule may be the same as or different from each other.

Another aspect of the present invention relates to a nonaqueous electrolyte solution containing the additive for nonaqueous electrolyte solutions, a nonaqueous solvent, and an electrolyte.

Yet another aspect of the present invention relates to an electricity storage device including the nonaqueous electrolyte solution, a positive electrode, and a negative electrode, a lithium ion battery, and a lithium ion capacitor.

The electricity storage device using the nonaqueous electrolyte solution containing the additive for nonaqueous electrolyte solutions can exhibit sufficiently low initial resistance and exhibit excellent cycle characteristics. In addition, gas generation after a long-term use of the electricity storage device can also be suppressed.

Advantageous Effects of Invention

According to the present invention, it is possible to provide an additive for nonaqueous electrolyte solutions, which makes it possible to suppress initial resistance, improve cycle characteristics over a long period of time, and suppress gas generation in a case where the additive for nonaqueous electrolyte solutions is used in an electricity storage device such as a nonaqueous electrolyte solution secondary battery. Further, it is also possible to provide a nonaqueous electrolyte solution using the additive for non-aqueous electrolyte solutions and an electricity storage device using the nonaqueous electrolyte solution.

BRIEF DESCRIPTION OF DRAWINGS

FIG. 1 is a schematic cross-sectional view showing one embodiment of a nonaqueous electrolyte solution secondary battery as an example of an electricity storage device.

DESCRIPTION OF EMBODIMENTS

The additive for nonaqueous electrolyte solutions according to one embodiment includes the compound represented by Formula (1a), the compound represented by Formula (1b), or a combination thereof.

X in Formulae (1a) and (1b) represents an alkylene group having 3 to 7 carbon atoms, which may be substituted, or an alkenylene group having 3 to 7 carbon atoms, which may be substituted, each of which constitutes a cyclic structure together with the sulfur atom of a sulfonyl group. In a case where X is an alkenylene group, the carbon atom adjacent to the sulfur atom of the sulfonyl group may form a double bond with a carbon atom adjacent thereto. From the viewpoint of further lowering the initial resistance, X may be an alkylene group having 3 to 7 carbon atoms, which may be substituted. From the viewpoint of lowering the battery resistance, X may be an alkylene group having 4 to 6 carbon atoms or an alkylene group having 4 carbon atoms (for example, an n-butane-1,4-diyl group). The alkylene group having 3 to 7 carbon atoms or the alkenylene group having 3 to 7 carbon atoms, which may be substituted, as X, may be further substituted with a substituent other than a substituent including Z. Examples of the substituent in that case include a halogen atom.

n in Formulae (1a) and (1b) represents an integer of 1 to 7. n pieces of sulfur atoms or nitrogen atoms may be respectively bonded to n pieces of carbon atoms in a cyclic sulfone constituted with a sulfonyl group and X. From the viewpoint of cycle characteristics, n may be an integer of 1 to 3.

In Formulae (1a) and (1b), Z represents a monovalent group represented by Formula (2a), (2b), or (2c). A plurality of Z's in the same molecule may be the same as or different from each other. From the viewpoint that the battery resistance is further lowered, Z may be a monovalent group represented by Formula (2a) including a sulfonyl group.

$R^{2a}$, $R^{2b}$, and $R^{2c}$ in Formulae (2a), (2b), and (2c) each independently represent an alkyl group having 1 to 4 carbon atoms, which may be substituted, an alkenyl group having 2 to 4 carbon atoms, which may be substituted, an alkynyl group having 2 to 4 carbon atoms, which may be substituted, an aryl group which may be substituted, an alkoxy group having 1 to 4 carbon atoms, which may be substituted, an alkenyloxy group having 2 to 4 carbon atoms, which may be substituted, an alkynyloxy group having 2 to 4 carbon atoms, which may be substituted, an aryloxy group which may be substituted, a hydroxyl group, a lithium alcoholate group, or a lithium atom, and two $R^{2c}$'s in the same molecule may be the same as or different from each other.

With regard to $R^{2a}$, $R^{2b}$, and $R^{2c}$, in a case where the alkyl group having 1 to 4 carbon atoms is substituted, the substituent may be, for example, a halogen atom. Examples of the alkyl group having 1 to 4 carbon atoms, which may be substituted with a halogen atom, include a methyl group, an ethyl group, an n-propyl group, an isopropyl group, an n-butyl group, an isobutyl group, a tert-butyl group, and a trifluoromethyl group. From the viewpoint that the battery resistance is further lowered, $R^{2a}$, $R^{2b}$, and $R^{2c}$ may be a methyl group, an ethyl group, a t-butyl group, or a methyl group.

With regard to $R^{2a}$, $R^{2b}$, and $R^{2c}$, in a case where the alkenyl group having 2 to 4 carbon atoms is substituted, the substituent may be, for example, a halogen atom. Examples of the alkenyl group having 2 to 4 carbon atoms, which may be substituted with a halogen atom, include a vinyl group, an allyl group, an isopropenyl group, a 1-butenyl group, a 2-butenyl group, a 3-butenyl group, an isobutenyl group, and a 1,1-difluoro-1-propenyl group. From the viewpoint that the battery resistance is further lowered, $R^{2a}$, $R^{2b}$, and $R^{2c}$ may be a vinyl group or an allyl group.

With regard to $R^{2a}$, $R^{2b}$, and $R^{2c}$, in a case where the alkynyl group having 2 to 4 carbon atoms is substituted, the substituent may be, for example, a halogen atom. Examples of the alkynyl group having 2 to 4 carbon atoms, which may be substituted with a halogen atom, include a 1-propynyl group, a 2-propynyl group, a 1-butynyl group, a 2-butynyl group, and a 3-butynyl group.

With regard to $R^{2a}$, $R^{2b}$, and $R^{2c}$, in a case where the aryl group is substituted, the substituent may be, for example, a halogen atom or an alkyl group having 1 to 3 carbon atoms (such as a methyl group). Examples of the aryl group which may be substituted with a halogen atom or an alkyl group having 1 to 3 carbon atoms include a phenyl group, a tolyl group, a xylyl group, and a naphthyl group.

With regard to $R^{2a}$, $R^{2b}$, and $R^{2c}$, in a case where the alkoxy group having 1 to 4 carbon atoms is substituted, the substituent may be, for example, a halogen atom. Examples of the alkoxy group which may be substituted with a halogen atom include a methoxy group, an ethoxy group, an n-propoxy group, and an n-butoxy group.

With regard to $R^{2a}$, $R^{2b}$, and $R^{2c}$, in a case where the alkenyloxy group having 2 to 4 carbon atoms is substituted, the substituent may be, for example, a halogen atom. Examples of the alkenyloxy group having 2 to 4 carbon atoms, which may be substituted with a halogen atom, include a 2-propenyloxy group, a 1-methyl-2-propenyloxy group, a 2-methyl-2-propenyloxy group, a 2-butenyloxy group, and a 3-butenyloxy group.

With regard to $R^{2a}$, $R^{2b}$, and $R^{2c}$, in a case where the alkynyloxy group having 2 to 4 carbon atoms, which may be substituted, the substituent may be, for example, a halogen atom. Examples of the alkynyloxy group having 2 to 4 carbon atoms, which may be substituted with a halogen atom, include a 2-propynyloxy group, a 1-methyl-2-propynyloxy group, a 2-methyl-2-propynyloxy group, a 2-butynyloxy group, and a 3-butynyloxy group.

With regard to $R^{2a}$, $R^{2b}$, and $R^{2c}$, in a case where the aryloxy group is substituted, the substituent may be, for example, an alkyl group having 1 to 3 carbon atoms, an alkoxy group having 1 to 3 carbon atoms, or a halogen atom. Examples of the alkyl group having 1 to 3 carbon atoms, the alkoxy group having 1 to 3 carbon atoms, or the aryloxy group which may be substituted with a halogen atom include a phenoxy group, a 2-methylphenoxy group, a 3-methylphenoxy group, a 4-methylphenoxy group, a 2-ethylphenoxy group, a 3-ethylphenoxy group, a 4-ethylphenoxy group, a 2-methoxyphenoxy group, a 3-methoxyphenoxy group, and a 4-methoxyphenoxy group.

With regard to $R^{2a}$, $R^{2b}$, and $R^{2c}$, examples of the halogen atom which can substitute the alkyl group having 1 to 4 carbon atoms, the alkenyl group having 2 to 4 carbon atoms, the alkynyl group having 2 to 4 carbon atoms, the aryl group, the alkoxy group having 1 to 4 carbon atoms, the alkenyloxy group having 2 to 4 carbon atoms, the alkynyloxy group having 2 to 4 carbon atoms, or the aryloxy group include an iodine atom, a bromine atom, and a fluorine atom. From the viewpoint the battery resistance is easily lowered, the halogen atom may be a fluorine atom.

From the viewpoint that the battery resistance is more easily lowered, $R^{2a}$, $R^{2b}$, and $R^{2c}$ may be, in particular, an alkyl group having 1 to 4 carbon atoms, which may be substituted with a halogen atom, an aryl group which may be substituted with a halogen atom, or an alkyl group having 1 to 3 carbon atoms, which may be substituted with a halogen atom.

In a case where X is an alkylene group having 4 carbon atoms (n-butane-1,4-diyl group), Formula (1a) may be, for example, Formula (1a-1). Z in Formula (1a-1) is the same as Z in Formula (1a).

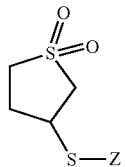

(1a-1)

Examples of the compound represented by Formula (1a-1) in which Z is a monovalent group represented by Formula (2a) include 3-methylsulfonylthiotetrahydrothiophene-1,1-dioxide, 3-ethylsulfonylthiotetrahydrothiophene-1,1-dioxide, 3-phenylsulfonylthiotetrahydrothiophene-1,1-dioxide, 3-trifluoromethylsulfonylthiotetrahydrothiophene-1,1-dioxide, 3-tert-butylsulfonylthiotetrahydrothiophene-1,1-dioxide, 3-methoxysulfonylthiotetrahydrothiophene-1,1-dioxide, 3-trifluoroethoxysulfonylthiotetrahydrothiophene-1,1-dioxide, 3-allylsulfonylthiotetrahydrothiophene-1,1-dioxide, and 3-lithiumoxysulfonylthiotetrahydrothiophene-1,1-dioxide.

Examples of the compound represented by Formula (1a-1) in which Z is a monovalent group represented by Formula (2b) include 3-methylcarbonylthiotetrahydrothiophene-1,1-dioxide, 3-ethylcarbonylthiotetrahydrothiophene-1,1-dioxide, 3-phenylcarbonylthiotetrahydrothiophene-1,1-dioxide, 3-trifluoromethylcarbonylthiotetrahydrothiophene-1,1-dioxide, 3-tert-butylcarbonylthiotetrahydrothiophene-1,1-dioxide, 3-methoxycarbonylthiotetrahydrothiophene-1,1-dioxide, and 3-trifluoroethoxycarbonylthiotetrahydrothiophene-1,1-dioxide.

Examples of the compound represented by Formula (1a-1) in which Z is a monovalent group represented by Formula (2c) include 3-dimethylphosphinylthiotetrahydrothiophene-1,1-dioxide, 3-diethylphosphinylthiotetrahydrothiophene-1,1-dioxide, 3-bis-trifluoromethylphosphinylthiotetrahydrothiophene-1,1-dioxide, 3-diphenylphosphinylthiotetrahydrothiophene-1,1-dioxide, 3-diallylphosphinylthiotetrahydrothiophene-1,1-dioxide, 3-divinylphosphinylthiotetrahydrothiophene-1,1-dioxide, 3-dipropargylphosphinylthiotetrahydrothiophene-1,1-dioxide, 3-dimethoxyphosphinylthiotetrahydrothiophene-1,1-dioxide, 3-diethoxyphosphinylthiotetrahydrothiophene-1,1-dioxide, 3-diphenoxyphosphinylthiotetrahydrothiophene-1,1-dioxide, 3-bis-trifluoromethoxyphosphinylthiotetrahydrothiophene-1,1-dioxide, 3-bis-allylphosphinylthiotetrahydrothiophene-1,1-dioxide, and 3-bis-cyclohexylphosphinylthiotetrahydrothiophene-1,1-dioxide.

In a case where X is an alkenylene group having 4 carbon atoms (1-butene-1,4-diyl group), Formula (1a) may be, for example, Formula (1a-2). Z in Formula (1a-2) is the same as Z in Formula (1a).

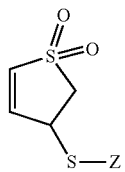

(1a-2)

Examples of the compound represented by Formula (1a-2) in which Z is a monovalent group represented by Formula (2a) include 4-methylsulfonylthiotetrahydrothiophene-1,1-dioxid-2-ene, 4-ethylsulfonylthiotetrahydrothiophene-1,1-dioxid-2-ene, 4-phenylsulfonylthiotetrahydrothiophene-1,1-dioxid-2-ene, 4-trifluoromethylsulfonylthiotetrahydrothiophene-1,1-dioxid-2-ene, 4-tert-butylsulfonylthiotetrahydrothiophene-1,1-dioxid-2-ene, 4-methoxysulfonylthiotetrahydrothiophene-1,1-dioxid-2-ene, 4-trifluoroethoxysulfonylthiotetrahydrothiophene-1,1-dioxid-2-ene, and 4-allylsulfonylthiotetrahydrothiophene-1,1-dioxid-2-ene.

Examples of the compound represented by Formula (1a-2) in which Z is a monovalent group represented by Formula (2b) include 4-methylcarbonylthiotetrahydrothiophene-1,1-dioxid-2-ene, 4-ethylcarbonylthiotetrahydrothiophene-1,1-dioxid-2-ene, 4-phenylcarbonylthiotetrahydrothiophene-1,1-dioxid-2-ene, 4-trifluoromethylcarbonylthiotetrahydrothiophene-1,1-dioxid-2-ene, 4-tert-butylcarbonylthiotetrahydrothiophene-1,1-dioxid-2-ene, 4-methoxycarbonylthiotetrahydrothiophene-1,1-dioxid-2-ene, and 4-trifluoroethoxycarbonyl- thiotetrahydrothiophene 1,1-dioxid-2-ene.

Examples of the compound represented by Formula (1a-2) in which Z is a monovalent group represented by Formula (2c) include 4-dimethylphosphinylthiotetrahydrothiophene-1,1-dioxid-2-ene, 4-diethylphosphinylthiotetrahydrothiophene-1,1-dioxid-2-ene, 4-bis-trifluoromethylphosphinylthiotetrahydrothiophene-1,1-dioxid-2-ene, 4-diphenylphosphinylthiotetrahydrothiophene-1,1-dioxid-2-ene, 4-diallylphosphinylthiotetrahydrothiophene-1,1-dioxid-2-ene, 4-divinylphosphinylthiotetrahydrothiophene-1,1-dioxid-2-ene, 4-dipropargylphosphinylthiotetrahydrothiophene-1,1-dioxid-2-ene, 4-dimethoxyphosphinylthiotetrahydrothiophene-1,1-dioxid-2-ene, 4-diethoxyphosphinylthiotetrahydrothiophene-1,1-dioxid-2-ene, 4-diphenoxyphosphinylthiotetrahydrothiophene-1,1-dioxid-2-ene, 4-bis-trifluoromethoxyphosphinylthiotetrahydrothiophene-1,1-dioxid-2-ene, 4-bis-allylphosphinylthiotetrahydrothiophene-1,1-dioxid-2-ene, 4-bis-cyclohexylphosphinylthiotetrahydrothiophene-1,1-dioxid-2-ene, and 4-lithiumoxyphosphinylthiotetrahydrothiophene-1,1-dioxid-2-ene.

In a case where X is an alkylene group having 4 carbon atoms (n-butane-1,4-diyl group), Formula (1b) may be, for example, Formula (1b-1), Z and m in Formula (1b-1) are the same as Z and m, respectively, in Formula (1b).

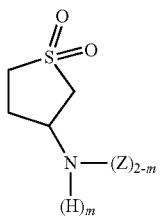

(1b-1)

Examples of the compound represented by Formula (1b-1) in which Z is a monovalent group represented by Formula (2a) and m is 1 include 3-(N-(methylsulfonyl)aminotetrahydrothiophene-1,1-dioxide, 3-(N-(ethylsulfonyl)aminotetrahydrothiophene-1,1-dioxide, 3-(N-(phenylsulfonyl)tetrahydrothiophene-1,1-dioxide, 3-(N-(trifluoromethylsulfonyl)aminotetrahydrothiophene-1,1-dioxide, and 3-(N-(allylsulfonyl)aminotetrahydrothiophene-1,1-dioxide.

Examples of the compound represented by Formula (1b-1) in which Z is a monovalent group represented by Formula (2b) and m is 1 include 3-(N-(methylcarbonyl)aminotetrahydrothiophene-1,1-dioxide, 3-(N-(ethylcarbonyl)aminotetrahydrothiophene-1,1-dioxide, 3-(N-(phenylcarbonyl)aminotetrahydrothiophene-1,1-dioxide, 3-(N-(trifluoromethylcarbonyl)aminotetrahydrothiophene-1,1-dioxide, and 3-(N-(methylcarbonyl)aminotetrahydrothiophene-1,1-dioxide.

Examples of the compound represented by Formula (1b-1) in which Z is a monovalent group represented by Formula (2c) and m is 1 include 3-(N-(dimethylphosphinyl)aminotetrahydrothiophene-1,1-dioxide, 3-(N-(diphenylphosphinyl)aminotetrahydrothiophene-1,1-dioxide, 3-(N-(vinylphosphinyl)aminotetrahydrothiophene-1,1-dioxide, 3-(N-(allylphosphinyl)aminotetrahydrothiophene-1,1-dioxide, 3-(N-(methoxyphosphinyl)aminotetrahydrothiophene-1,1-dioxide, and 3-(N-(lithiumoxyphosphinyl)aminotetrahydrothiophene-1,1-dioxide.

Examples of the compound represented by Formula (1b-1) in which Z is a monovalent group represented by Formula (2a) and m is 0 include 3-(N,N-bis-(methylsulfonyl)aminotetrahydrothiophene-1,1-dioxide, 3-(N,N-bis-(methylsulfonyl)aminotetrahydrothiophene-1,1-dioxide, 3-(N,N-bis-(ethylsulfonyl)aminotetrahydrothiophene-1,1-dioxide, 3-(N,N-bis-(phenylsulfonyl)tetrahydrothiophene-1,1-dioxide, 3-(N,N-bis-(trifluoromethylsulfonyl)aminotetrahydrothiophene-1,1-dioxide, 3-(N,N-bis-(allylsulfonyl)aminotetrahydrothiophene-1,1-dioxide, 3-(N,N-bis-(methylcarbonyl)aminotetrahydrothiophene-1,1-dioxide, and 3-(N,N-bis-bis(lithiumoxysulfonyl)aminotetrahydrothiophene-1,1-dioxide.

Examples of the compound represented by Formula (1b-1) in which Z is a monovalent group represented by Formula (2b) and m is 0 include 3-(N,N-bis-(ethylcarbonyl)aminotetrahydrothiophene-1,1-dioxide, 3-(N,N-bis-(phenylcarbonyl)aminotetrahydrothiophene-1,1-dioxide, 3-(N,N-bis-(trifluoromethylcarbonyl)aminotetrahydrothiophene-1,1-dioxide, and 3-(N,N-bis-(methylcarbonyl)aminotetrahydrothiophene-1,1-dioxide.

Examples of the compound represented by Formula (1b-1) in which Z is a monovalent group represented by Formula (2c) and m is 0 include 3-(N,N-bis-(dimethylphosphinyl)aminotetrahydrothiophene-1,1-dioxide, 3-(N,N-bis-(diphenylphosphinyl)aminotetrahydrothiophene-1,1-dioxide, 3-(N,N-bis-(vinylphosphinyl)aminotetrahydrothiophene-1,1-dioxide, 3-(N,N-bis-(allylphosphinyl)aminotetrahydrothiophene-1,1-dioxide, and 3-(N,N-bis-(methoxyphosphinyl)aminotetrahydrothiophene-1,1-dioxide.

In a case where X is an alkenylene group having 4 carbon atoms (1-butene-1,4-diyl group), Formula (1b) may be, for example, Formula (1b-2). Z and m in Formula (1b-2) are the same as Z and m, respectively, in Formula (1b).

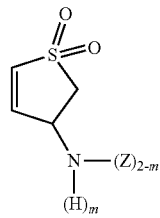

(1b-2)

Examples of the compound represented by Formula (1b-2) in which Z is a monovalent group represented by Formula (2a) and m is 1 include 4-(N-(methylsulfonyl)aminotetrahydrothiophene-1,1-dioxid-2-ene, 4-(N-(methylsulfonyl)aminotetrahydrothiophene-1,1-dioxid-2-ene, 4-(N-(ethylsulfonyl)aminotetrahydrothiophene-1,1-dioxid-2-ene, 4-(N-(phenylsulfonyl)aminotetrahydrothiophene-1,1-dioxid-2-ene, 4-(N-(trifluoromethylsulfonyl)aminotetrahydrothiophene-1,1-dioxid-2-ene, and 4-(N-(allylsulfonyl)aminotetrahydrothiophene-1,1-dioxid-2-ene.

Examples of the compound represented by Formula (1b-2) in which Z is a monovalent group represented by Formula (2b) and m is 1 include 4-(N-(methylcarbonyl)aminotetrahydrothiophene-1,1-dioxid-2-ene, 4-(N-(ethylcarbonyl)aminotetrahydrothiophene-1,1-dioxid-2-ene, 4-(N-(phenylcarbonyl)aminotetrahydrothiophene-1,1-dioxid-2-ene, 4-(N-(trifluoromethylcarbonyl)aminotetrahydrothiophene-1,1-dioxid-2-ene, and 4-(N-(methylcarbonyl)aminotetrahydrothiophene-1,1-dioxid-2-ene.

Examples of the compound represented by Formula (1b-2) in which Z is a monovalent group represented by Formula (2c) and m is 1 include 4-(N-(dimethylphosphinyl)aminotetrahydrothiophene-1,1-dioxid-2-ene, 4-(N-(diphenylphosphinyl)aminotetrahydrothiophene-1,1-dioxid-2-ene, 4-(N-(vinylphosphinyl)aminotetrahydrothiophene-1,1-dioxid-2-ene, 4-(N-(allylphosphinyl)aminotetrahydrothiophene-1,1-dioxid-2-ene, 4-(N-(methoxyphosphinyl)aminotetrahydrothiophene-1,1-dioxid-2-ene, and 4-(N-(lithiumoxyphosphinyl)aminotetrahydrothiophene-1,1-dioxid-2-ene.

Examples of the compound represented by Formula (1b-2) in which Z is a monovalent group represented by Formula (2a) and m is 0 include 4-(N,N-bis-(methylsulfonyl)aminotetrahydrothiophene-1,1-dioxid-2-ene, 4-(N,N-bis-(methylsulfonyl)aminotetrahydrothiophene-1,1-dioxid-2-ene, 4-(N,N-bis-(ethylsulfonyl)aminotetrahydrothiophene-1,1-dioxid-2-ene, 4-(N,N-bis-(phenylsulfonyl)aminotetrahydrothiophene-1,1-dioxid-2-ene, 4-(N,N-bis-(trifluoromethylsulfonyl)aminotetrahydrothiophene-1,1-dioxid-2-ene, and 4-(N,N-bis-(allylsulfonyl)aminotetrahydrothiophene-1,1-dioxid-2-ene.

Examples of the compound represented by Formula (1b-2) in which Z is a monovalent group represented by Formula (2b) and m is 0 include 4-(N,N-bis-(methylcarbonyl)aminotetrahydrothiophene-1,1-dioxid-2-ene, 4-(N,N-bis-(ethylcarbonyl)aminotetrahydrothiophene-1,1-dioxid-2-ene, 4-(N,N-bis-(phenylcarbonyl)aminotetrahydrothiophene-1,1-dioxid-2-ene, 4-(N,N-bis-(trifluoromethylcarbonyl)aminotetrahydrothiophene-1,1-dioxid-2-ene, and 4-(N,N-bis-(methylcarbonyl)aminotetrahydrothiophene-1,1-dioxid-2-ene.

Examples of the compound represented by Formula (1b-2) in which Z is a monovalent group represented by Formula (2c) and m is 0 include 4-(N,N-bis-(dimethylphosphinyl)aminotetrahydrothiophene-1,1-dioxid-2-ene, 4-(N,N-bis-(diphenylphosphinyl)aminotetrahydrothiophene-1,1-dioxid-2-ene, 4-(N,N-bis-(vinylphosphinyl)aminotetrahydrothiophene-1,1-dioxid-2-ene, 4-(N,N-bis-(allylphosphinyl)aminotetrahydrothiophene-1,1-dioxid-2-ene, 4-(N,N-bis-(methoxyphosphinyl)aminotetrahydrothiophene-1,1-dioxid-2-ene, and 4-(N,N-bis-(lithiumoxyphosphinyl)aminotetrahydrothiophene-1,1-dioxid-2-ene.

The compound represented by Formula (1a) or (1b) can be synthesized by using available raw materials and combining ordinary reactions thereof. For example, the compound of Formula (1a) in which X is an alkylene group having 4 carbon atoms (n-butane-1,4-diyl group), Z is a monovalent group represented by Formula (2a), and n is 1 can be synthesized, for example, by reacting 3-mercaptosulfolane with a sulfonyl chloride derivative such as methanesulfonyl chloride, paratoluenesulfonyl chloride, benzenesulfonyl chloride, and trifluoromethanesulfonyl chloride. Further, the compound of Formula (1b) in which X is an alkylene group having 4 carbon atoms (n-butane-1,4-diyl group), Z is a monovalent group represented by Formula (2a), m is 1, and n is 1 can be synthesized by, for example, the same method as above, except that 3-aminosulfolane is used instead of 3-mercaptosulfolane.

A nonaqueous electrolyte solution according to one embodiment contains the compound represented by Formula (1a) or (1b) as an additive for nonaqueous electrolyte solutions, a nonaqueous solvent, and an electrolyte. This additive for nonaqueous electrolyte solutions is prepared, for example, by dissolving the compound represented by Formula (1a) or (1b) in a nonaqueous solvent together with an electrolyte.

The additive for nonaqueous electrolyte solutions according to the present embodiment may include only one kind or two or more kinds of the compounds represented by Formula (1a) or (1b). The additive for nonaqueous electrolyte solutions according to the present embodiment may further include a cyclic carbonate compound, a nitrile compound, an isocyanate compound, a C≡C group-containing compound, an S=O group- or S(=O)$_2$ group-containing compound (other than the compound represented by Formula (1a) or (1b)), a phosphorus-containing compound, an acid anhydride, a cyclic phosphazene compound, a boron-containing compound, a silicon-containing compound, or the like, as desired.

Examples of the cyclic carbonate compound include 4-fluoro-1,3-dioxolan-2-one (FEC), trans- or cis-4,5-difluoro-1,3-dioxolan-2-one (DFEC), vinylene carbonate (VC), vinyl ethylene carbonate (VEC), and 4-ethynyl-1,3-dioxolan-2-one (EEC). As the cyclic carbonate compound, VC, FEC, VEC, or a combination thereof may be used.

Examples of the nitrile compound include acetonitrile, propionitrile, succinonitrile, glutaronitrile, adiponitrile, pimelonitrile, suberonitrile, and sebaconitrile. As the nitrile compound, succinonitrile, adiponitrile, or a combination thereof may be used.

Examples of the isocyanate compound include methyl isocyanate, ethyl isocyanate, butyl isocyanate, phenyl isocyanate, tetramethylene diisocyanate, hexamethylene diisocyanate, octamethylene diisocyanate, 1,4-phenylene diisocyanate, 2-isocyanatoethyl acrylate, and 2-isocyanatoethyl methacrylate.

Examples of the C≡C group-containing compound include 2-propynyl methyl carbonate, 2-propynyl acetate, 2-propynyl formate, 2-propynyl methacrylate, 2-propynyl methanesulfonate, 2-propynyl vinylsulfonate, 2-propynyl 2-(methanesulfonyloxy)propionate, di(2-propynyl)oxalate, methyl-2-propynyl oxalate, ethyl-2-propynyl oxalate, di(2-propynyl)glutarate, 2-butyne-1,4-diyl dimethanesulfonate, 2-butyne-1,4-diyl diformate, and 2,4-hexadiyne-1,6-diyl dimethanesulfonate.

Examples of the S=O group- or S(=O)$_2$ group-containing compound include sultones such as 1,3-propanesultone (PS), 1,3-butanesultone, 2,4-butanesultone, 1,4-butanesultone, 1,3-propenesultone, 2,2-dioxide-1,2-oxathiolan-4-yl acetate, and 5,5-dimethyl-1,2-oxathiolan-4-one 2,2-dioxide, cyclic sulfites such as ethylene sulfite, ethylene sulfate, hexahydrobenzo[1,3,2]dioxathiolan-2-oxide (also referred to as 1,2-cyclohexanediolcyclic sulfite), and 5-vinyl-hexahydro-1,3,2-benzodioxathiol-2-oxide, sulfonic acid esters such as butane-2,3-diyl dimethanesulfonate, butane-1,4-diyl dimethanesulfonate, methylenemethane disulfonate, and 1,3-propanedisulfonic acid anhydride, divinylsulfone, 1,2-bis(vinylsulfonyl)ethane, and bis(2-vinylsulfonylethyl) ether.

Examples of the phosphorus-containing compound include trimethyl phosphate, tributyl phosphate, trioctyl phosphate, tris(2,2,2-trifluoroethyl) phosphate, bis(2,2,2-trifluoroethyl)methyl phosphate, bis(2,2,2-trifluoroethyl)ethyl phosphate, bis(2,2,2-trifluoroethyl)2,2-difluoroethyl phosphate, bis(2,2,2-trifluoroethyl)2,2,3,3-tetrafluoropropyl phosphate, bis(2,2-difluoroethyl)2,2,2-trifluoroethyl phosphate, bis(2,2,3,3-tetrafluoropropyl)2,2,2-trifluoroethyl phosphate, and (2,2,2-trifluoroethyl)(2,2,3,3-tetrafluoropropyl)methyl phosphate, tris(1,1,1,3,3,3-hexafluoropropan-2-yl) phosphate, methyl methylenebisphosphonate, ethyl methylenebisphosphonate, methyl ethylenebisphosphonate, ethyl ethylenebisphosphonate, methyl butylenebisphosphonate, ethyl butylenebisphosphonate, methyl 2-(dimethylphosphoryl)acetate, ethyl 2-(dimethylphosphoryl)acetate, methyl 2-(diethylphosphoryl)acetate, ethyl 2-(diethylphosphoryl)acetate, 2-propynyl 2-(dimethylphosphoryl)acetate, 2-propynyl 2-(diethylphosphoryl)acetate, methyl 2-(dimethoxyphosphoryl)acetate, ethyl 2-(dimethoxyphosphoryl)acetate, methyl 2-(diethoxyphosphoryl)acetate, ethyl 2-(diethoxyphosphoryl)acetate, 2-propynyl 2-(dimethoxyphosphoryl)acetate, 2-propynyl 2-(diethoxyphosphoryl)acetate, methyl pyrophosphate, and ethyl pyrophosphate.

Examples of the acid anhydride include acetic anhydride, propionic anhydride, succinic anhydride, maleic anhydride, 3-allyl succinic anhydride, glutaric anhydride, itaconic anhydride, and 3-sulfo-propionic anhydride.

Examples of the cyclic phosphazene compound include methoxypentafluorocyclotriphosphazene, ethoxypentafluorocyclotriphosphazene, phenoxypentafluorocyclotriphosphazene, and ethoxyheptafluorocyclotetraphosphazene.

Examples of the silicon-containing compound include, hexamethylcyclotrisiloxane, hexaethylcyclotrisiloxane, hexaphenylcyclotrisiloxane, 1,3,5-trimethyl-1,3,5-trivinylcyclotrisiloxane, octamethylcyclotetrasiloxane, decamethylcyclopentasiloxane, trimethylfluorosilane, triethylfluorosilane, tripropylfluorosilane, phenyldimethylfluorosilane, triphenylfluorosilane, vinyldimethylfluorosilane, vinyldiethylfluorosilane, vinyldiphenylfluorosilane, trimethoxyfluorosilane, triethoxyfluorosilane, dimethyldifluorosilane, diethyldifluorosilane, divinyldifluorosilane, ethylvinyldifluorosilane, methyltrifluorosilane, ethyltrifluorosilane, hexamethyldisiloxane, 1,3-diethyltetramethyldisiloxane, hexaethyldisiloxane, octamethyltrisiloxane, methoxytrimethylsilane, ethoxytrimethylsilane, dimethoxydimethylsilane, trimethoxymethylsilane, tetramethoxysilane, bis(t-rimethylsilyl)peroxide, trimethylsilyl acetate, triethylsilyl acetate, trimethylsilyl propionate, trimethylsilyl methacrylate, trimethylsilyl trifluoroacetate, trimethylsilyl methanesulfonate, trimethylsilyl ethanesulfonate, triethylsilyl methanesulfonate, trimethylsilyl fluoromethanesulfonate, bis(trimethylsilyl) sulfate, tris(trimethylsiloxy)boron, tris(trimethylsilyl) phosphate, and tris(trimethylsilyl)phosphite.

Examples of the boron-containing compound include boroxine, trimethylboroxine, trimethoxyboroxine, triethylboroxine, triethoxyboroxine, tri-isopropylboroxine, tri-isopropoxyboroxine, tri-n-propylboroxine, tri-n-propoxyboroxine, tri-n-butylboroxine, tri-n-butyroxyboroxine, triphenylboroxine, triphenoxyboroxine, tricyclohexylboroxine and tricyclohexoxyboroxine.

The nonaqueous electrolyte solution according to the present embodiment contains the additive for nonaqueous electrolyte solutions, a nonaqueous solvent, and an electrolyte.

The content of the additive (or the compound represented by (1a) or (1b)) for nonaqueous electrolyte solutions in the nonaqueous electrolyte solution may be 0.005% to 10% by mass in terms of a total amount with respect to the total mass of the nonaqueous electrolyte solution. In a case where the content of the additive for nonaqueous electrolyte solutions is 0.005% by mass or more, more excellent battery characteristics can be obtained, and in a case where the content is 10% by mass or less, it is difficult for the viscosity of the nonaqueous electrolyte solution to be increased, whereby the ion mobility can be sufficiently secured. From the same viewpoint, the content of the additive (or the compound represented by (1a) or (1b)) for nonaqueous electrolyte solutions may be in the range of 0.01% to 10% by mass in terms of a total amount with respect to the total mass of the nonaqueous electrolyte solution.

In a case where the compound represented by Formula (1a) or (1b) and the cyclic carbonate compound are used in combination as the additive, the content of the cyclic carbonate compound may be 0.001% to 10% by mass with respect to the total mass of the nonaqueous electrolyte solution. In a case where the content of the cyclic carbonate compound is within this range, the SEI does not become too thick and the stability of the SEI at a higher temperature is increased.

The content of the cyclic carbonate compound may be 0.01% by mass or more, or 0.5% by mass or more, with respect to the total mass of the nonaqueous electrolyte solution.

In a case where the compound represented by Formula (1a) or (1b) and the nitrile compound are used in combination as the additive, the content of the nitrile compound may be 0.001% to 10% by mass with respect to the total mass of the nonaqueous electrolyte solution. In a case where the content of the nitrile compound is within this range, the SEI does not become too thick and the stability of SEI at a higher temperature is increased. The content of the nitrile compound may be 0.01% by mass or more, or 0.5% by mass or more, with respect to the total mass of the nonaqueous electrolyte solution.

In a case where the compound represented by Formula (1a) or (1b) and the isocyanate compound are used in combination as the additive, the content of the isocyanate compound may be 0.01% to 5% by mass, with respect to the total mass of the nonaqueous electrolyte solution. In a case where the content of the isocyanate compound is within this range, the SEI does not become too thick and the stability of the SEI at a higher temperature is increased. In a case where the content of the isocyanate compound may be 0.5% by mass or more, or 3% by mass or less, with respect to the total mass of the nonaqueous electrolyte solution.

In a case where the compound represented by Formula (1a) or (1b) and the C≡C group-containing compound are used in combination as the additive, the content of the C≡C group-containing compound may be 0.01% to 5% by mass with respect to the total mass of the nonaqueous electrolyte solution. In a case where the content of the C≡C group-containing compound is within this range, the SEI does not become too thick and the stability of the SEI at a higher temperature is increased. The content of the C≡C group-containing compound is 0.1% by mass or more, with respect to the total mass of the nonaqueous electrolyte solution.

In a case where the compound represented by Formula (1a) or (1b) and the S=O group- or S(=O)$_2$ group-containing compound are used in combination as the additive, a content of the S=O group- or S(=O)$_2$ group-containing compound may be 0.001% to 5% by mass with respect to the total mass of the nonaqueous electrolyte solution. In a case where the content of the S=O group- or S(=O)$_2$ group-containing compound is within this range, the SEI does not become too thick and the stability of the SEI at a higher temperature is increased. The content of the S=O group- or S(=O)$_2$ group-containing compound may be 0.01% by mass or more, or 0.1% by mass or more, with respect to the total mass of the nonaqueous electrolyte solution.

In a case where the compound represented by Formula (1a) or (1b) and the phosphorus-containing compound are used in combination as the additive, the content of the phosphorus-containing compound may be 0.001% to 5% by mass with respect to the total mass of the nonaqueous electrolyte solution. In a case where the content of the phosphorus-containing compound is within this range, the SEI does not become too thick and the stability of the SEI at a higher temperature is increased. The content of the phosphorus-containing compound may be 0.01% by mass or more, or 0.1% by mass or more, with respect to the total mass of the nonaqueous electrolyte solution.

In a case where the compound represented by Formula (1a) or (1b) and the cyclic phosphazene compound are used in combination as the additive, the content of the cyclic phosphazene compound may be 0.001% to 5% by mass with respect to the total mass of the nonaqueous electrolyte solution. In a case where the content of the cyclic phosphazene compound is within this range, the SEI does not become too thick and the stability of the SEI at a higher temperature is increased. The content of the cyclic phosphazene compound may be 0.010% by mass or more, or 0.1% by mass or more, with respect to the total mass of the nonaqueous electrolyte solution.

In a case where the compound represented by Formula (1a) or (1b) and the acid anhydride are used in combination as the additive, the content of the acid anhydride may be 0.001% to 5% by mass with respect to the total mass of the nonaqueous electrolyte solution. In a case where the content of the acid anhydride is within this range, the SEI does not become too thick and the stability of the SEI at a higher temperature is increased. The content of the acid anhydride may be 0.01% by mass or more, or 0.5% by mass or more, with respect to the total mass of the nonaqueous electrolyte solution.

In a case where the compound represented by Formula (1a) or (1b) and the boron-containing compound are used in combination as the additive, the content of the boron-containing compound may be 0.001% to 5% by mass with respect to the total mass of the nonaqueous electrolyte solution. With the content within this range, the SEI does not become too thick and the stability of the SEI at a higher temperature is increased. The content of the boron-containing compound may be 0.01% by mass or more, or 0.1% by mass or more, with respect to the total mass of the nonaqueous electrolyte solution.

In a case where the compound represented by Formula (1a) or (1b) and the silicon-containing compound are used in combination as the additive, the content of the silicon-containing compound may be 0.01% to 5% by mass with respect to the total mass of the nonaqueous electrolyte solution. In a case where the content of the silicon-containing compound is within this range, the SEI does not become too thick and the stability of the SEI at a higher temperature is increased. The content of the silicon-containing compound may be 0.1% by mass or more, or 0.5% by mass or more, with respect to the total mass of the nonaqueous electrolyte solution.

From the viewpoints that the viscosity of a nonaqueous electrolyte solution thus obtained is suppressed to a lower value, an aprotic solvent can be selected as the nonaqueous solvent. The aprotic solvent may be at least one selected from the group consisting of a cyclic carbonate, a chained carbonate, an aliphatic carboxylic acid ester, a lactone, a lactam, a cyclic ether, a chained ether, a sulfone, a nitrile, and a halogen derivative thereof. As the aprotic solvent, the cyclic carbonate or the chained carbonate can be selected from, and a combination of the cyclic carbonate and the chained carbonate can also be selected as the aprotic solvent.

Examples of the cyclic carbonate include ethylene carbonate, propylene carbonate, and butylene carbonate. The 4-fluoro-1,3-dioxolan-2-one (FEC) exemplified as the cyclic carbonate of the additive may be used as the nonaqueous solvent. Examples of the chained carbonate include dimethyl carbonate, diethyl carbonate, and ethyl methyl carbonate. Examples of the aliphatic carboxylic acid ester include methyl acetate, ethyl acetate, methyl propionate, ethyl propionate, methyl butyrate, methyl isobutyrate, and methyl trimethylacetate. Examples of the lactone include γ-butyrolactone. Examples of the lactam include ε-caprolactam and N-methylpyrrolidone. Examples of the cyclic ether include tetrahydrofuran, 2-methyltetrahydrofuran, tetrahydropyran, and 1,3-dioxolane. Examples of the chained ether include 1,2-diethoxyethane and ethoxymethoxyethane. Examples of the sulfone include sulfolane. Examples of the nitrile include acetonitrile. Acetonitrile may be used as the additive or the nonaqueous solvent. Examples of the halogen derivative include 4-chloro-1,3-dioxolan-2-one and 4,5-difluoro-1,3-dioxolan-2-one. These nonaqueous solvents may be used alone or as a mixture of a plurality of kinds thereof.

The electrolyte may be a lithium salt which serves as an ion source of lithium ions. The electrolyte may be at least one selected from the group consisting of LiAlCl$_4$, LiBF$_4$, LiPF$_6$, LiClO$_4$, LiAsF$_6$, and LiSbF$_6$. It is preferable that LiBF$_4$ and/or LiPF$_6$ may be selected as the electrolyte from the viewpoints that it has a high degree of dissociation, can enhance the ion conductivity of the electrolyte solution, and has an action of suppressing deterioration of the performance of an electricity storage device by a long-term use due to their oxidation-reduction resistance characteristics. These electrolytes may be used alone or in combination of two or more kinds thereof.

In a case where the electrolyte is LiBF$_4$ and/or LiPF$_6$, one or more of each of cyclic carbonates and chained carbonates may be combined as the nonaqueous solvent. In particular, LiBF$_4$ and/or LiPF$_6$, ethylene carbonate, and diethyl carbonate may be combined.

The concentration of the electrolyte in the nonaqueous electrolyte solution may be 0.1 to 2.0 mol/L with respect to the volume of the nonaqueous electrolyte solution. In a case where the concentration of the electrolyte is 0.1 mol/L or more, more excellent discharge characteristics, charge characteristics, and the like are obtained. In a case where the concentration of the electrolyte is 2.0 mol/L or less, it is difficult for the viscosity of the nonaqueous electrolyte solution to be increased, whereby the ion mobility can be secured at a higher level. From the same viewpoint, the concentration of the electrolyte may be 0.5 to 1.5 mol/L.

In the nonaqueous electrolyte solution according to the present embodiment, a second lithium salt that is different from the electrolyte (a first lithium salt) may also be used in combination. Examples of the second lithium salt include lithium salts having a phosphoric acid skeleton, such as lithium difluorophosphate, lithium bisoxalatoborate (LiBOB), lithium tetrafluoro(oxalato)phosphate (LiTFOP), lithium difluorooxalatoborate (LiDFOB), lithium difluorobisoxalatophosphate (LiDFOP), lithium tetrafluoroborate, lithium bisfluorosulfonylimide, lithium tetrafluoro(oxalato) phosphate, and $Li_2PO_3F$; and lithium salts having an $S(=O)$ group, such as lithium trifluoro((methanesulfonyl)oxy)borate, lithium pentafluoro((methanesulfonyl)oxy)phosphate, lithium methylsulfate, lithium ethylsulfate, lithium 2,2,2-trifluoroethylsulfate, and lithium fluorosulfonate. The second lithium salt may include one or more lithium salts selected from the group consisting of lithium difluorophosphate, lithium bisoxalatoborate, lithium tetrafluoro(oxalato) phosphate, lithium difluorooxalate borate, lithium difluorobisoxalate phosphate, lithium methylsulfate, lithium ethyl sulfate, and lithium fluorosulfonate.

The concentration of the second lithium salt in the nonaqueous electrolyte solution may be 0.001 to 1.0 mol/L with respect to the volume of the nonaqueous electrolyte solution. In a case where the concentration of the second lithium salt is 0.001 mol/L or more, more excellent charge/discharge characteristics are obtained under a high-temperature condition. In a case where the concentration of the second lithium salt is 1.0 mol/L or less, it is difficult for the viscosity of the nonaqueous electrolyte solution to be increased, whereby the ion mobility can be sufficiently secured. From the same viewpoint, the concentration of the second lithium salt may be 0.01 to 0.8 mol/L, or may be 0.01 to 0.5 mol/L.

The nonaqueous electrolyte solution according to the present embodiment is prepared by adding an additive for nonaqueous electrolyte solutions, including the compound represented by Formula (1a) or (1b), to a nonaqueous solvent in which an electrolyte and a common additive substance to be added as desired are dissolved.

The nonaqueous electrolyte solution according to the present embodiment can be used as an electrolyte solution of an electricity storage device including a positive electrode and a negative electrode. For example, in a case where the nonaqueous electrolyte solution containing the additive for nonaqueous electrolyte solutions according to the present embodiment is used in a nonaqueous electrolyte solution secondary battery such as a lithium ion battery, or an electricity storage device such as an electric double layer capacitor such as a lithium ion capacitor, it is possible to improve cycle characteristics over a long period of time, suppress initial resistance, and suppress an increase in long-term resistance. In addition, the additive for nonaqueous electrolyte solutions can also suppress gas generation in a case where the electricity storage device is stored at a high temperature for a long period of time.

FIG. 1 is a schematic cross-sectional view showing one embodiment of a nonaqueous electrolyte solution secondary battery as an example of an electricity storage device. A nonaqueous electrolyte solution secondary battery 1 shown in FIG. 1 includes a positive electrode plate 4 (positive electrode), a negative electrode plate 7 (negative electrode), a nonaqueous electrolyte solution 8 disposed between the positive electrode plate 4 and the negative electrode plate 7, and a separator 9 provided in the nonaqueous electrolyte solution 8. The positive electrode plate 4 has a positive electrode collector 2 and a positive electrode active material layer 3 provided on the side of the nonaqueous electrolyte solution 8. The negative electrode plate 7 has a negative electrode collector 5 and a negative electrode active material layer 6 provided on the side of the nonaqueous electrolyte solution 8. As the nonaqueous electrolyte solution 8, the nonaqueous electrolyte solution according to the above-mentioned embodiment can be used. Although FIG. 1 shows the nonaqueous electrolyte solution secondary battery as the electricity storage device, an electricity storage device obtained by application of the nonaqueous electrolyte solution is not limited thereto, and it may be another electricity storage device such as an electric double layer capacitor.

As the positive electrode collector 2 and the negative electrode collector 5, for example, a metal foil formed of a metal such as aluminum, copper, nickel, and stainless steel can be used.

The positive electrode active material layer 3 includes a positive electrode active material. The positive electrode active material may be a lithium-containing composite oxide. Examples of the lithium-containing composite oxide include lithium-containing composite oxides such as $LiMnO_2$, $LiFeO_2$, $LiCoO_2$, $LiMn_2O_4$, $Li_2FeSiO_4$, $LiNi_{1/3}Co_{1/3}Mn_{1/3}O_2$, $LiNi_{0.5}Co_{0.2}Mn_{0.3}O_2$, $LiNi_{0.6}Co_{0.2}Mn_{0.2}O_2$, $LiNi_{0.8}Co_{0.1}Mn_{0.1}O_2$, $LiNi_xCo_yM_zO_2$ (provided that $0.01<x<1$, $0\leq y\leq 1$, $0\leq z\leq 1$, and $x+y+z=1$ are satisfied, and M is at least one element selected from the group consisting of Mn, V, Mg, Mo, Nb, Fe, Cu, and Al), $LiFePO_4$, $LiNi_{0.8}Co_{0.15}Al_{0.05}O_2$.

The negative electrode active material layer 6 includes a negative electrode active material. Examples of the negative electrode active material include a material capable of absorbing and releasing lithium. Examples of such a material include carbon materials such as crystalline carbon (natural graphite, artificial graphite, and the like), amorphous carbon, carbon-coated graphite, and resin-coated graphite, oxide materials such as indium oxide, silicon oxide, tin oxide, lithium titanate, zinc oxide, and lithium oxide, and metal materials such as a lithium metal and a metal capable of forming an alloy together with lithium. Examples of the metal capable of forming an alloy together with lithium include Cu, Sn, Si, Co, Mn, Fe, Sb, and Ag, and a binary or ternary alloy including some of these metals and lithium can also be used as the negative electrode active material. These negative electrode active materials may be used alone or in mixture of two or more kinds thereof.

From the viewpoint of achieving a higher energy density, a carbon material such as graphite and an Si-based active material such as Si, an Si alloy, and an Si oxide may be combined. From the viewpoint of achieving both of the cycle characteristics and the higher energy density, graphite and the Si-based active material may be combined as the negative electrode active material. With regard to such a combination, the mass ratio of the Si-based active material to the total mass of the carbon material and the Si-based active material may be from 0.5% by mass to 95% by mass, from 1% by mass to 50% by mass, or from 2% by mass to 40% by mass.

The positive electrode active material layer 3 and the negative electrode active material layer 6 may further include a binder. Examples of the binder include polyvinylidene difluoride (PVdF), a vinylidene fluoride-hexafluoropropylene copolymer, a vinylidene fluoride-tetrafluoroethylene copolymer, a styrene-butadiene copolymerized rubber, carboxymethyl cellulose, polytetrafluoroethylene, polypropylene, polyethylene, polyimide, polyamideimide, polyacrylic acid, polyvinyl alcohol, acrylic acid-polyacrylonitrile, polyacrylamide, polymethacrylic acid, and a copolymer thereof. The binders may be the same as or different from each other in the positive electrode active material layer and the negative electrode active material layer.

The positive electrode active material layer 3 and the negative electrode active material layer 6 may further include a conductive auxiliary material for the purpose of lowering the resistance. Examples of the conductive auxiliary material include carbonaceous fine particles such as graphite, carbon black, acetylene black, and Ketjen black, and carbon fibers.

As the separator 9, for example, a single-layer or laminate microporous film formed of polyethylene, polypropylene, a fluorine resin, or the like, or a woven fabric or nonwoven fabric porous film can be used.

Specific forms such as a shape and a thickness of each of members constituting the electricity storage device can be set as appropriate by those skilled in the art. The configurations of the electricity storage device are not limited to the aspect of FIG. 1 and modifications can be made as appropriate.

EXAMPLES

Hereinafter, the present invention will be described more specifically with reference to Examples. However, the present invention is not limited to these Examples.

1. Synthesis of Additive (Compound Represented by Formula (1a) or (1b)) for Nonaqueous Electrolyte Solutions Synthesis of Compound 1 (3-Methylsulfonylthiotetrahydrothiophene-1,1-dioxide)

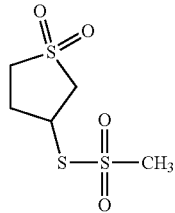

(1-1)

50 mL of dichloromethane was charged into a 300-mL four-necked flask equipped with a stirrer, a cooling pipe, a thermometer, and a dropping funnel. 3-Mercaptosulfolane (1.52 g, 10 mmol) and triethylamine (0.972 g, 12 mmol) were added thereto while cooling in an ice bath. Then, after methanesulfonyl chloride (1.24 g, 10 mmol) was added dropwise thereto, the reaction solution in the flask was heated to 40° C. and the reaction solution was stirred for 40 hours while maintaining the temperature. The reaction solution was cooled to room temperature and 50 mL of water was added thereto. Then, the reaction solution was cooled to 0° C., and the precipitated solid was taken out by filtration and dried to obtain Compound 1 (0.48 g) represented by Formula (1-1). The yield of Compound 1 was 21% with respect to 3-mercaptosulfolane. It was confirmed by an LC/MS spectrum that the molecular weight of the obtained Compound 1 was 230.

Synthesis of Compound 2 (3-(N-(Methylsulfonyl)Aminotetrahydrothiophene-1,1-Dioxide)

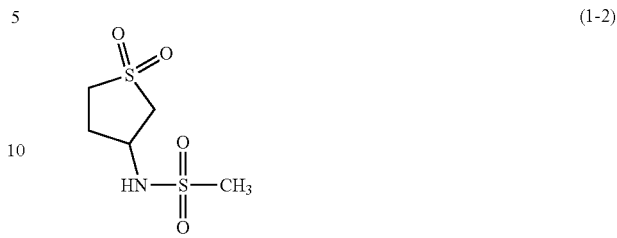

(1-2)

Compound 2 (0.89 g) represented by Formula (1-2) was obtained by the same reaction as in the synthesis of Compound 1, except that 3-mercaptosulfolane was changed to 3-aminosulfolane (1.35 g, 10 mmol). The yield of Compound 2 was 42% with respect to 3-aminosulfolane. It was confirmed by an LC/MS spectrum that the molecular weight of the obtained Compound 2 was 213.

Synthesis of Compound 3 (3-(N-(Methylcarbonyl)Amninotetrahydrothiophene-1,1-Dioxide)

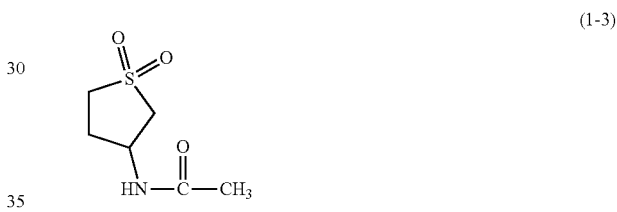

(1-3)

Compound 3 (0.75 g) represented by Formula (1-3) was obtained by the same reaction as in the synthesis of Compound 2 except that methanesulfonyl chloride was changed to acetyl chloride (0.79 g, 10 mmol). The yield of Compound 3 was 52% with respect to 3-aminosulfolane. It was confirmed by an LC/MS spectrum that the molecular weight of the obtained compound 3 was 177.

Synthesis of Compound 4 (4-Methylsulfonylthiotetrahydrothiophene-1,1-Dioxide-2-Ene)

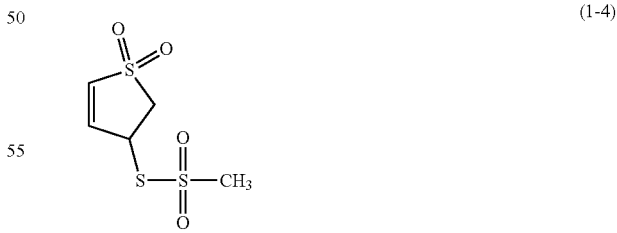

(1-4)

Compound 4 represented by Formula (1-4) was obtained by the same reaction as in the synthesis of Compound 1, except that 3-mercaptosulfolane was changed to 4-amino-2-sulfolene (0.79 g, 10 mmol). The yield of Compound 4 was 32% with respect to 4-amino-2-sulfolene. It was confirmed by an LC/MS spectrum that the molecular weight of the obtained compound 4 was 228.

2. Preparation of Nonaqueous Electrolyte Solution

Examples 1 to 4

Ethylene carbonate (EC) and diethyl carbonate (DEC) were mixed at a compositional volume ratio of EC:DEC=30:70 to prepare a nonaqueous mixed solvent. $LiPF_6$ as an electrolyte was dissolved in the nonaqueous mixed solvent to a concentration of 1.0 mol/L. Compound 1 as an additive for nonaqueous electrolyte solutions was added to the obtained solution to prepare a nonaqueous electrolyte solution of Example 1. The concentration of the additive (Compound 1) for nonaqueous electrolyte solutions was set to 1.0% by mass with respect to the total mass of the nonaqueous electrolyte solution. Nonaqueous electrolyte solutions of Examples 2 to 4 were prepared in the same manner, except that Compound 2, 3 or 4 was used instead of Compound 1.

Comparative Example 1

A nonaqueous electrolyte solution was prepared in the same manner as in Example 1, except that Compound 1 was not used.

Comparative Example 2

A nonaqueous electrolyte solution was prepared in the same manner as in Example 1, except that 1,3-propanesultone (PS) (manufactured by Tokyo Chemical Industry Co., Ltd.) was used instead of Compound 1.

Comparative Example 3

A nonaqueous electrolyte solution was prepared in the same manner as in Example 1, except that vinylene carbonate (VC) (manufactured by Tokyo Chemical Industry Co., Ltd.) was used instead of Compound 1.

Comparative Example 4

A nonaqueous electrolyte solution was prepared in the same manner as in Example 1, except that fluoroethylene carbonate (FEC) (manufactured by Tokyo Chemical Industry Co., Ltd.) was used instead of Compound 1.

3. Manufacture of Nonaqueous Electrolyte Solution Secondary Battery (Manufacture of Nonaqueous Electrolyte Solution Secondary Battery)

$LiNi_{1/3}Co_{1/3}Mn_{1/3}O_2$ as a positive electrode active material and carbon black as an electrical conductivity-imparting agent were dry-mixed. A mixture thus obtained was uniformly dispersed in N-methyl-2-pyrrolidone (NMP), in which polyvinylidene difluoride (PVDF) as a binder had been dissolved, to prepare a slurry. A slurry thus obtained was applied onto both surfaces of an aluminum metal foil (rectangular, thickness: 20 μm), NMP was removed from the coating film by evaporation, and then the whole film was pressed to manufacture a positive electrode sheet having the aluminum metal foil as a positive electrode collector and positive electrode active material layers formed on both surfaces thereof. The ratio of the solid contents in the obtained positive electrode sheet was set to positive electrode active material:electrical conductivity-imparting agent: PVDF=92:5:3 in terms of a mass ratio.

Graphite powder as a negative electrode active material was uniformly dispersed in water including a styrene-butadiene rubber (SBR) as a binder and carboxymethyl cellulose (CMC) as a thickener to prepare a slurry. The obtained slurry was applied to one surface of a copper foil (rectangular, thickness: 10 μm). Water was removed from the coating film and the whole film was then pressed to obtain a negative electrode sheet having the copper foil as a negative electrode collector and a negative electrode active material layer formed on one surface thereof. The ratio of the solid contents in the negative electrode sheet was set to negative electrode active material:CMC:SBR=98:1:1 in terms of a mass ratio.

The manufactured positive electrode sheets and negative electrode sheets were laminated together with separators in the order of the negative electrode sheet, the separator, the positive electrode sheet, the separator, and the negative electrode sheet to manufacture a battery element. A polyethylene film was used as the separator. This battery element was put into a bag formed of a laminated film having an aluminum foil (thickness: 40 μm) and resin layers coating both surfaces thereof in such a way that the terminals of the positive electrode sheet and the negative electrode sheet protruded from the bag. Subsequently, each of the nonaqueous electrolyte solutions obtained in Examples and Comparative Examples was poured into the bag. The bag was vacuum-sealed to obtain a sheet-shaped nonaqueous electrolyte solution secondary battery. Further, in order to increase the adhesiveness between the electrodes, the sheet-shaped nonaqueous electrolyte solution secondary battery was sandwiched between glass plates and pressurized.

4. Evaluation

Initial Resistance Ratio

The obtained nonaqueous electrolyte solution secondary battery was charged to 4.2 V with a current corresponding to 0.2 C at 25° C., and then the nonaqueous electrolyte solution secondary battery was kept at 45° C. for 24 hours. Thereafter, the nonaqueous electrolyte solution secondary battery was discharged to 3 V with a current corresponding to 0.2 C at 25° C. Subsequently, the nonaqueous electrolyte solution secondary battery was stabilized by aging in which charging up to 4.2 V with a current corresponding to 0.2 C and discharging up to 3 V with a current corresponding to 0.2 C were alternately repeated for 3 cycles. Then, after performing the initial charge/discharge with 1 C, a discharge capacity of the nonaqueous electrolyte solution secondary battery was measured and this value was defined as an "initial capacity".

In addition, with regard to the nonaqueous electrolyte solution secondary battery which had been charged to a capacity of 50% of the initial capacity after the initial charge/discharge, an AC impedance at 25° C. was measured and this value was defined as an initial resistance (Ω). Here, the "initial resistance ratio" is a relative value of the resistance of each nonaqueous electrolyte solution secondary battery in a case where the initial resistance (Ω) of Comparative Example 1 is taken as 1.

Cycle Characteristics (Discharge Capacity Maintenance Rate and Resistance Increase Rate)

With regard to each of the nonaqueous electrolyte solution secondary batteries after the initial charge/discharge, a charge/discharge cycle test with 200 cycles was performed under the conditions of a charge rate of 1 C, a discharge rate of 1 C, a charge cut-off voltage of 4.2 V, and a discharge cut-off voltage of 3 V. Thereafter, a discharge capacity of the nonaqueous electrolyte solution secondary battery was measured by performing charging/discharging with 1 C and defined as "a discharge capacity after the 200-cycle test".

In addition, after the cycle test, with regard to the nonaqueous electrolyte solution secondary battery which had been charged to a capacity to 50% of the discharge capacity after the 200-cycle test, an AC impedance in an environment at 25° C. was measured and this value was defined as "a resistance (Ω) after the 200-cycle test". Here, the "discharge capacity maintenance rate" and the "resistance increase rate" are values calculated by the following equations.

Discharge capacity maintenance rate (%)=(Discharge capacity after 200-cycle test/Initial capacity)×100

Resistance increase rate (%)=(Resistance after 200-cycle test/Initial resistance)×100

Amount of Gas Generated

Apart from the batteries used for evaluation of the initial resistance, and evaluation of the discharge capacity maintenance rate and the resistance increase rate, a nonaqueous electrolyte solution secondary battery having the same configuration including each of the electrolyte solutions of Examples and Comparative Examples was prepared. This nonaqueous electrolyte solution secondary battery was charged to 4.2 V with a current corresponding to 0.2 C at 25° C. and then aged by keeping it at 45° C. for 24 hours. Thereafter, the nonaqueous electrolyte solution secondary battery was discharged to 3 V with a current corresponding to 0.2 C at 25° C. Subsequently, the nonaqueous electrolyte solution secondary battery was subjected to repetition of three cycles of an operation of charging to 4.2 V with a current corresponding to 0.2 C and discharging to 3 V with a current corresponding to 0.2 C to perform initial charge/discharge, thereby stabilizing the nonaqueous electrolyte solution battery.

The volume of the nonaqueous electrolyte solution secondary battery after the initial charge/discharge was measured by an Archimedes' method and this value was defined as an initial volume (cm³) of the battery. Furthermore, the nonaqueous electrolyte solution secondary battery was charged to 4.2 V with a current corresponding to 1 C at 25° C. and then kept at 60° C. for 168 hours. Thereafter, the nonaqueous electrolytic secondary battery was cooled to 25° C. and then discharged to 3 V with a current corresponding to 1 C. The volume of the nonaqueous electrolyte solution secondary battery after the discharge was measured by an Archimedes' method and this value was defined as a volume (cm³) of the battery after a high-temperature storage. The amount of gas generated was calculated by the following equation.

Amount of gas generated=(Volume after storage at high temperature)−(Initial volume)

TABLE 1

| Additive | Conc. (% by mass) | Initial resistance ratio | Discharge capacity maintenance rate (%) | Resistance increase rate (%) | Amt. of gas generated (cm³) |
|---|---|---|---|---|---|
| Ex. 1 | Cpd. 1 | 1.0 | 0.65 | 93 | 1.3 | 0.22 |
| Ex. 2 | Cpd. 2 | 1.0 | 0.78 | 92 | 1.3 | 0.28 |
| Ex. 3 | Cpd. 3 | 1.0 | 0.68 | 91 | 1.2 | 0.33 |
| Ex. 4 | Cpd. 4 | 1.0 | 0.84 | 93 | 1.1 | 0.23 |
| Comp. Ex. 1 | — | — | 1 | 85 | 1.5 | 0.38 |
| Comp. Ex. 2 | PS | 1.0 | 0.86 | 89 | 1.3 | 0.35 |
| Comp. Ex. 3 | VC | 1.0 | 1.18 | 89 | 1.4 | 0.30 |
| Comp. Ex. 4 | FEC | 1.0 | 0.88 | 88 | 1.4 | 0.44 |

The evaluation results of the respective nonaqueous electrolyte solution secondary batteries are shown in Table 1. It was confirmed that in the nonaqueous electrolyte solution secondary batteries of Examples, including the nonaqueous electrolyte solution including the compound represented by Formula (1a) or (1b), the initial resistance is suppressed, excellent cycle characteristics are exhibited for a long period of time, and gas generation was suppressed.

REFERENCE SIGNS LIST

1 . . . Electricity storage device (Nonaqueous electrolyte solution secondary battery), 2 . . . Positive electrode collector, 3 . . . Positive electrode active material layer, 4 . . . Positive electrode plate, 5 . . . Negative electrode collector, 6 . . . Negative electrode active material layer, 7 . . . Negative electrode plate, 8 . . . Nonaqueous electrolyte

The invention claimed is:

1. An additive for nonaqueous electrolyte solutions comprising a compound represented by the following formula (1a) or (1b):

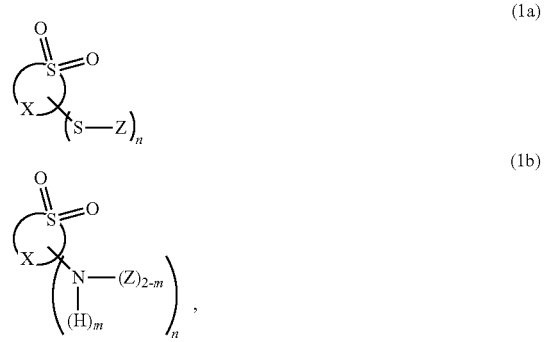

wherein in Formulae (1a) and (1b), X represents an alkylene group having 3 to 7 carbon atoms without substitution, or an alkenylene group having 3 to 7 carbon atoms, which may be substituted, each of which constitutes a cyclic structure together with the sulfur atom of a sulfonyl group, n represents an integer of 1 to 7, Z represents a monovalent group represented by Formula (2a), and m represents 0 or 1:

wherein $R^{2a}$ represents an alkyl group having 1 to 4 carbon atoms, which may be substituted, an alkenyl group having 2 to 4 carbon atoms, which may be substituted, an alkynyl group having 2 to 4 carbon atoms, which may be substituted, an aryl group which may be substituted, an alkoxy group having 1 to 4 carbon atoms, which may be substituted, an alkenyloxy group having 2 to 4 carbon atoms, which may be substituted, an alkynyloxy group having 2 to 4 carbon atoms, which may be substituted, an aryloxy group which may be substituted, a hydroxyl group, a lithium alcoholate group, or a lithium atom.

2. A nonaqueous electrolyte solution comprising:
an additive for nonaqueous electrolyte solutions;
a nonaqueous solvent; and
an electrolyte,
   wherein the additive for nonaqueous electrolyte solutions comprises a compound represented by the following formula (1a) or (1b):

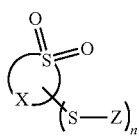

(1a)

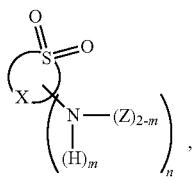

(1b)

in Formulae (1a) and (1b), X represents an alkylene group having 3 to 7 carbon atoms which may be substituted, or an alkenylene group having 3 to 7 carbon atoms, which may be substituted, each of which constitutes a cyclic structure together with the sulfur atom of a sulfonyl group, n represents an integer of 1 to 7, Z represents a monovalent group represented by Formula (2a), (2b), or (2c), and m represents 0 or 1:

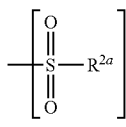

(2a)

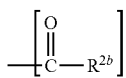

(2b)

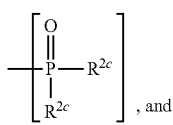

(2c)

, and in Formulae (2a), (2b), and (2c), $R^{2a}$, $R^{2b}$, and $R^{2c}$ each independently represent an alkyl group having 1 to 4 carbon atoms, which may be substituted, an alkenyl group having 2 to 4 carbon atoms, which may be substituted, an alkynyl group having 2 to 4 carbon atoms, which may be substituted, an aryl group which may be substituted, an alkoxy group having 1 to 4 carbon atoms, which may be substituted, an alkenyloxy group having 2 to 4 carbon atoms, which may be substituted, an alkynyloxy group having 2 to 4 carbon atoms, which may be substituted, an aryloxy group which may be substituted, a hydroxyl group, a lithium alcoholate group, or a lithium atom, and two $R^{2c}$'s in the same molecule may be the same as or different from each other.

3. The nonaqueous electrolyte solution according to claim 2, wherein the nonaqueous solvent includes a cyclic carbonate and a chained carbonate.

4. The nonaqueous electrolyte solution according to claim 2, wherein the electrolyte includes a lithium salt.

5. An electricity storage device comprising:
the nonaqueous electrolyte solution according to claim 2;
a positive electrode; and
a negative electrode.

6. A lithium ion battery comprising:
the nonaqueous electrolyte solution according to claim 2;
a positive electrode; and
a negative electrode.

7. A lithium ion capacitor comprising:
the nonaqueous electrolyte solution according to claim 2;
a positive electrode; and
a negative electrode.

8. A nonaqueous electrolyte solution comprising:
an additive for nonaqueous electrolyte solutions;
a nonaqueous solvent; and
an electrolyte,
   wherein the additive for nonaqueous electrolyte solutions comprises a compound represented by the following formula (1a) or (1b):

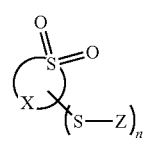

(1a)

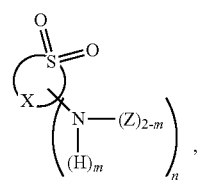

(1b)

wherein in Formulae (1a) and (1b), X represents an alkylene group having 3 to 7 carbon atoms without substitution, or an alkenylene group having 3 to 7 carbon atoms, which may be substituted, each of which constitutes a cyclic structure together with the sulfur atom of a sulfonyl group, n represents an integer of 1 to 7, Z represents a monovalent group represented by Formula (2a), (2b), or (2c), and m represents 0 or 1:

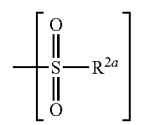

(2a)

-continued

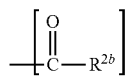   (2b)

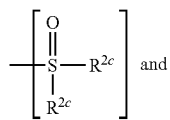 and   (2c)

in Formulae (2a), (2b), and (2c), $R^{2a}$, $R^{2b}$, and $R^{2c}$ each independently represent an alkyl group having 1 to 4 carbon atoms, which may be substituted, an alkenyl group having 2 to 4 carbon atoms, which may be substituted, an alkynyl group having 2 to 4 carbon atoms, which may be substituted, an aryl group which may be substituted, an alkoxy group having 1 to 4 carbon atoms, which may be substituted, an alkenyloxy group having 2 to 4 carbon atoms, which may be substituted, an alkynyloxy group having 2 to 4 carbon atoms, which may be substituted, an aryloxy group which may be substituted, a hydroxyl group, a lithium alcoholate group, or a lithium atom, and two $R^{2c}$'s in the same molecule may be the same as or different from each other.

9. The nonaqueous electrolyte solution according to claim 8, wherein the nonaqueous solvent includes a cyclic carbonate and a chained carbonate.

10. The nonaqueous electrolyte solution according to claim 8, wherein the electrolyte includes a lithium salt.

11. An electricity storage device comprising:
the nonaqueous electrolyte solution according to claim 8;
a positive electrode; and
a negative electrode.

12. A lithium ion battery comprising:
the nonaqueous electrolyte solution according to claim 8;
a positive electrode; and
a negative electrode.

13. A lithium ion capacitor comprising:
the nonaqueous electrolyte solution according to claim 8;
a positive electrode; and
a negative electrode.

* * * * *